United States Patent
Peterson et al.

(10) Patent No.: US 6,410,783 B1
(45) Date of Patent: Jun. 25, 2002

(54) METHOD OF PRODUCING CARBOXYLIC ACID SALTS

(75) Inventors: Rodger E. Peterson, Beaumont, TX (US); Terrance M. Cannan, Raleigh, NC (US); Rudolph E. Lisa, Grosse Ile, MI (US)

(73) Assignee: BASF Corporation, Mt. Olive, NJ (US)

( * ) Notice: Subject to any disclaimer, the term of this patent is extended or adjusted under 35 U.S.C. 154(b) by 0 days.

(21) Appl. No.: 09/692,119

(22) Filed: Oct. 19, 2000

(51) Int. Cl.$^7$ .................. C07C 63/00; C07C 63/33; C07C 63/337; C07C 63/44; C07C 63/04
(52) U.S. Cl. ................... 562/405; 562/493
(58) Field of Search .................... 562/493

(56) References Cited

U.S. PATENT DOCUMENTS

| | | |
|---|---|---|
| 2,637,639 A | 5/1953 | Talbot et al. |
| 2,945,051 A | 7/1960 | Davis |
| 3,012,870 A | 12/1961 | Richter |
| 3,013,054 A | 12/1961 | Richter |
| 3,287,404 A | 11/1966 | Hanna |
| 3,376,327 A | 4/1968 | Freeland |
| 3,444,192 A | 5/1969 | Newcomer |
| 3,723,090 A | 3/1973 | Houlihan |
| 3,827,404 A | 8/1974 | North |
| 3,910,974 A | 10/1975 | Hokama |
| 3,923,849 A | 12/1975 | Hokama |
| 4,161,611 A | 7/1979 | Kim |
| 4,223,154 A | 9/1980 | Liu et al. |
| 4,294,771 A | 10/1981 | Pietralla et al. |
| 4,297,509 A | 10/1981 | Chlasson |
| 4,307,027 A | 12/1981 | Borzelli et al. |
| 4,650,338 A | 3/1987 | List et al. |
| 4,772,434 A | 9/1988 | Myers |
| 4,824,257 A | 4/1989 | List et al. |
| 4,826,324 A | 5/1989 | Kunz et al. |
| 4,889,431 A | 12/1989 | Liechti |
| 4,941,130 A | 7/1990 | List et al. |
| 4,950,081 A | 8/1990 | List |
| 5,070,197 A | 12/1991 | Chin et al. |
| 5,121,992 A | 6/1992 | List et al. |
| 5,147,135 A | 9/1992 | List et al. |
| 5,266,553 A | 11/1993 | Champion et al. |
| 5,274,144 A | 12/1993 | Wuest et al. |
| 5,277,832 A | 1/1994 | Gill et al. |
| 5,407,266 A | 4/1995 | Dötsch et al. |
| 5,468,720 A | 11/1995 | Lisa et al. |
| 5,823,674 A | 10/1998 | Liechti et al. |
| 5,934,801 A | 8/1999 | List et al. |
| 5,939,584 A * | 8/1999 | Merkle et al. ............ 562/471 |
| 6,039,469 A | 3/2000 | Palmer |

FOREIGN PATENT DOCUMENTS

| | | |
|---|---|---|
| EP | 0 430 325 A1 | 6/1991 |
| GB | 988.074 | 4/1965 |
| GB | 1.021893 | 3/1966 |

OTHER PUBLICATIONS

Publication entitled *Reactions* from http://www.listgrp.com/reaction.htm, dated Nov. 3, 1999.

* cited by examiner

*Primary Examiner*—Paul J. Killos
*Assistant Examiner*—Zachary Tucker
(74) *Attorney, Agent, or Firm*—Alston & Bird LLP

(57) ABSTRACT

The present invention is a method of producing dry, alkali metal or ammonium carboxylic acid salt particles. In accordance with the invention, a molten carboxylic acid is mixed with a solution of an alkali metal-containing or ammonium-containing alkaline compound and the carboxylic acid and alkaline compound are reacted to form the carboxylic acid salt. Water is then removed from the carboxylic acid salt to produce dry, carboxylic acid salt particles. The feed ratio of the molten carboxylic acid and the alkaline compound is controlled to neutralize the carboxylic acid in the process.

27 Claims, 1 Drawing Sheet

METHOD OF PRODUCING CARBOXYLIC ACID SALTS

FIELD OF THE INVENTION

The present invention relates to the preparation of dry, carboxylic acid salt particles and particularly to methods of neutralizing carboxylic acids using alkali metal-containing or ammonium-containing alkaline compounds to produce safe and useful herbicidal carboxylic acid salts.

BACKGROUND OF THE INVENTION

Carboxylic acids such as benzoic acids, phenoxy carboxylic acids, pyridine carboxylic acids and quinoline carboxylic acids have been found to be useful in controlling the growth of weeds in various crops. In particular, these carboxylic acids are classified as growth regulator herbicides and act as synthetic auxins in preventing the growth of weeds in crops. A herbicidally effective amount of these carboxylic acid herbicides is applied to the locus of the weeds generally with agriculturally acceptable carriers, surfactants and other additives to control the growth of the weeds.

Because the carboxylic acid herbicides are generally insoluble in water, the carboxylic acids have traditionally been converted to their ester or salt forms for application to weed loci. In these forms, the carboxylic acids can be transported as concentrated solutions and then diluted for actual use. For example, the carboxylic acid esters are generally provided as petroleum distillate-based emulsifiable concentrates and the carboxylic acid salts are typically provided as aqueous concentrates, both of which are diluted with water for actual use.

The carboxylic acid salts have become the preferred forms for these herbicides. In particular, the ammonium and alkali metal salts are commonly used to control the growth of broadleaf weeds. In addition to providing these carboxylic acid salts as liquid concentrates, these carboxylic salts can also be provided in granular form.

The conventional method of preparing granular carboxylic acid salts is to mix and react an aqueous carboxylic acid solution and an alkali metal- or ammonium-containing alkaline solution to produce the carboxylic acid salt and water. The carboxylic acid salt is then dried to form either a liquid concentrate or the granular herbicide.

One problem with this conventional method is cost. In particular, to dry the carboxylic acid salt after its formation, the salt must be heated. Because of the volume of water that is used to form the solution and produced during the formation of the carboxylic acid salt, it is expensive to provide the necessary amount of heat energy to dry the carboxylic acid salt solution to form the liquid concentrate or granular herbicide.

Furthermore, there may be complications associated with conventional dryers used to dry carboxylic acid salt solutions. For example, although spray dryers are commonly used to dry these solutions, the amount of water that needs to be added to the solution often must be increased to allow for effective atomization of the feed. Additionally, because extra water is often needed, the inlet gas temperatures required to dry the material economically may exceed the safe operating temperature of the material. As a result, the dryers must be operated to avoid the risk of fire or explosion of the product. The spray dryer is either operated at the higher desired temperature with an inert atmosphere, which is expensive, or the spray dryer is operated at low and safe temperatures, which substantially reduces the production rate.

Another issue related to the production of carboxylic acid salts is the pH of the carboxylic acid salt solution. Various methods have been employed to control the pH of the carboxylic acid salt solution and the resulting carboxylic acid salts. In particular, because the resulting carboxylic acid salts are generally later dissolved in water for their eventual use, it is important to have salts that produce a desirable pH when dissolved in water.

One method of controlling the pH of the carboxylic acid salt solution is to neutralize the solution as needed prior to drying the carboxylic acid salts. For example, buffers such as alkaline compounds have been combined with the carboxylic acid salts to produce the desired pH for the carboxylic acid solution. U.S. Pat. No. 5,266,553 describes a method of producing carboxylic acid salts by forming the carboxylic acid salts from the carboxylic acid and an alkaline compound and then reacting the carboxylic acid salt with a second alkaline buffer compound to produce a carboxylic acid salt having increased water volubility.

An alternative method of controlling the pH of the salts is to prepare different batches of carboxylic acid salts and to mix the batches to provide the desired pH. However, it is difficult to dry process salts, particularly when they are sticky, to produce a consistent product.

Using buffers and blending salt batches are not efficient methods of producing granular carboxylic acid salt herbicides. Therefore, there is a need in the art to provide a method of consistently producing dry, carboxylic acid salts.

SUMMARY OF THE INVENTION

The present invention provides a method for consistently producing dry, carboxylic acid salts. In the production of these salts by the present method, the carboxylic acid is substantially fully neutralized. As a result, the carboxylic acid salts of the invention do not require blending or the use of buffers to produce a desired pH. Therefore, the carboxylic acid salts produced according to the invention can be immediately packaged and transported for use. Furthermore, the carboxylic acid salts of the invention can also be produced at a lower cost because of reduced heating costs in their formation.

The benefits of the present invention are provided by a method of preparing an alkali metal or an ammonium carboxylic acid salt by feeding a molten carboxylic acid and an alkali metal-containing or ammonium-containing alkaline compound in solution to a mixer and mixing the carboxylic acid and alkaline compound. Preferably, the alkaline compound is fed to the mixer in an amount within about 1%, and preferably within 0.6%, of the molar amount sufficient to neutralize the carboxylic acid fed to the mixer. Preferably, the molten carboxylic acid is also substantially free of water. The molten carboxylic acid and the alkali metal-containing or ammonium-containing alkaline compound react to form an alkali metal or ammonium carboxylic acid salt and the carboxylic acid is substantially neutralized, i.e., less than about 1% of the carboxylic acid fed to the process remains after the reacting step. At least a portion of the reacting step and typically substantially all of the reacting step occurs in the mixer. The carboxylic acid salt and any remaining carboxylic acid and alkaline compound are advanced from the mixer to a dryer where water (formed by the reaction and fed with the alkaline compound) is removed from the alkali metal or ammonium carboxylic acid salt to produce dry, alkali metal or ammonium carboxylic acid salt particles. The dry, alkali metal or ammonium carboxylic acid salt particles are then recovered as product and do not require buffers or batch mixing to adjust the pH of the particles. The method steps of the invention typically form a portion of a continuous process for making carboxylic acid salts.

In accordance with the invention, the carboxylic acids used in the method of preparing carboxylic acid salts are preferably growth regulating herbicides selected from the group consisting of benzoic acid herbicides, phenoxy carboxylic acid herbicides, pyridine carboxylic acid herbicides and quinoline carboxylic acid herbicides. 2-Methoxy-3,6-dichlorobenzoic acid (dicamba) is particularly preferred for use in the invention. The alkali metal-containing or ammonium-containing alkaline compound is preferably a sodium compound such as sodium hydroxide or sodium bicarbonate.

In one preferred embodiment of the invention, the molten carboxylic acid and the solution of the alkali metal-containing or ammonium-containing alkaline compound are metered to the mixer. In accordance with the invention, it is preferred that the ratio of the feed components are maintained such that the amount of alkaline compound metered to the mixer or the dryer is consistently within about 1% of the molar amount sufficient to neutralize the carboxylic acid. At least a portion of the reaction and typically substantially all of the reaction occurs in the mixer such that less than about 1% of the carboxylic acid fed to the mixer is advanced to the dryer. The mixer and dryer are preferably both insulated so that any heat of neutralization produced in the reacting step can be used to aid in removing water from the resulting carboxylic acid salt. The dryer is also preferably heated to produce the dry, carboxylic acid salt particles and can be operated under a vacuum, in a nitrogen atmosphere, or both. The dryer is also preferably self-cleaning especially when the resulting carboxylic acid salt solutions strongly adhere to the hot dryer surfaces, i.e., are sticky. The resulting dry, carboxylic acid salt particles include preferably less than 5% and more preferably less than 1% water by weight.

In another preferred embodiment of the invention, sodium dicambate is prepared by mixing molten dicamba with an aqueous sodium hydroxide solution at a molar ratio of 1:0.97+/−0.6%, i.e., at a ratio of between 1:0.964 and 1:0.976, and preferably at a substantially constant molar ratio between 1:0.964 to 1:0.976. Preferably, the molten dicamba is substantially free of water. The molten dicamba and the solution of the alkaline sodium compound are preferably fed to a mixer and then advanced to a dryer. The molten dicamba and the alkaline sodium compound are reacted to produce the sodium salt of dicamba (sodium dicambate) and the dicamba is substantially neutralized. Water is then removed from the sodium dicambate to produce dry, sodium dicambate particles having a pH, when dissolved in water, of between about 7 and about 9. The dry, sodium dicambate particles are then recovered as product.

The method of the invention can produce dry, carboxylic acid salts without the need for an additional or second neutralization step. In addition, the process of the invention is particularly useful for materials that strongly adhere to the hot dryer surfaces such as sodium dicambate in that the use of a mixer and dryer in combination produces carboxylic acid salts having a consistent pH. Furthermore, unlike prior art methods that use carboxylic acids dissolved in water, the molten carboxylic acid that is used in the method of the invention is essentially free of water thus reducing the amount of water that must be removed in drying. This in turn reduces the cost of drying the carboxylic acid salts. The resulting dry, carboxylic acid salts are at a desired pH (when dissolved in water) and can be immediately packaged and transported without having to blend the salts or buffer the salts to provide the desired pH.

These and other features and advantages of the present invention will become more readily apparent to those skilled in the art upon consideration of the following detailed description and accompanying drawing, which describe both the preferred and alternative embodiments of the present invention.

DETAILED DESCRIPTION OF THE PREFERRED EMBODIMENTS

Figure 1:
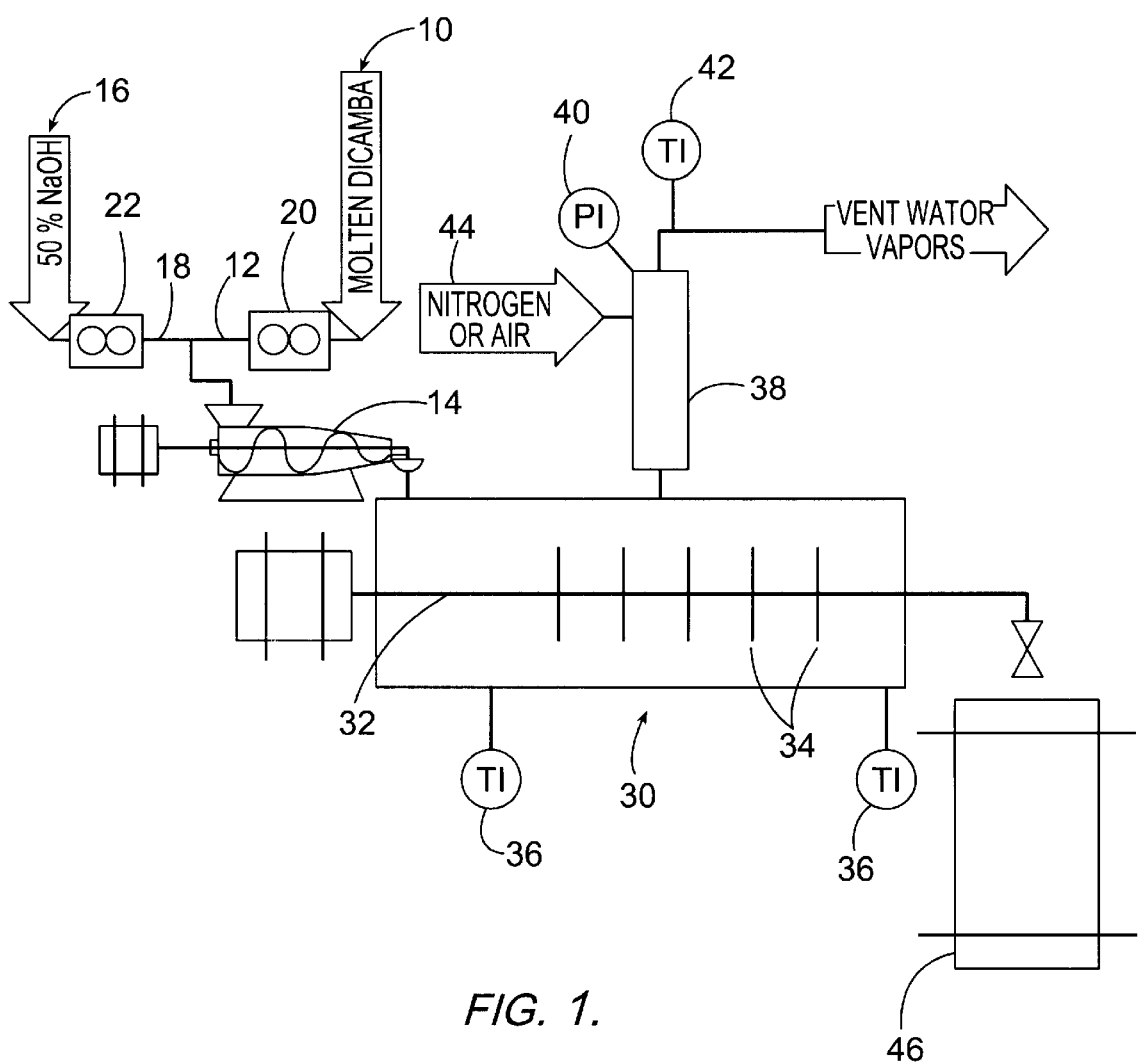
FIG. 1 schematically illustrates an exemplary method of preparing carboxylic acid salts according to the invention.

In the drawings and the following detailed description, preferred embodiments are described in detail to enable practice of the invention. Although the invention is described with reference to these specific preferred embodiments, it will be understood that the invention is not limited to these preferred embodiments. To the contrary, the invention includes numerous alternatives, modifications and equivalents as will become apparent from consideration of the following detailed description and accompanying drawing.

FIG. 1 schematically illustrates an exemplary method for producing carboxylic acid salts in accordance with the present invention. In FIG. 1, molten carboxylic acid is fed from a molten carboxylic acid source 10 through a feedline 12 into a mixer, designated generally as 14. The molten carboxylic acid can be loaded continuously or intermittently to mixer 14, preferably using a pump as described in more detail below.

The molten carboxylic acid is prepared by heating a solid carboxylic acid under conditions sufficient to form a melt thereof. As will be appreciated by the skilled artisan, conditions for providing a molten carboxylic acid can vary depending upon factors such as the melting point of the carboxylic acid, viscosity of the acid melt, flow rate, pressure, and the like. For example, the carboxylic acid 2-methoxy-3,6-dichlorobenzoic acid (dicamba) has a melting point of about 105° C. In the invention, dicamba is heated to a temperature sufficient to melt the acid so that it is flowable but not so high that the acid decomposes. Preferably dicamba is heated to a temperature no greater than about 130° C., and more preferably to a temperature between about 105° C. to about 115° C. One skilled in the art can readily determine the appropriate temperature ranges for other carboxylic acids.

Feedline 12 can be traced so that the temperature is sufficient to maintain the carboxylic acid in its molten state. For example, feedline 12 can be traced electrically or by heating the feedline by methods known in the art such as using steam or a jacket with oil or high pressure steam. When using dicamba, feedline 12 is typically maintained at a temperature ranging from about 105° C. to about 115° C.

An alkaline compound is fed from an alkaline compound source 16 through a feedline 18 to mixer 14. The alkaline compound can also be loaded continuously or intermittently to mixer 14, for example using a pump as described in more detail below. The alkaline compound can be in solid or liquid form or as a solid dissolved or dispersed in solvent. Advantageously, the alkaline compound is provided in solution and preferably in an aqueous solution. When an aqueous solution is used, the concentration of the alkaline compound can vary, and is typically from about 20 to about 80 percent, preferably about 50 percent, although concentrations outside this range can also be used.

The carboxylic acid can include any herbicidal compound including carboxylic acid functionality as known in the art. Exemplary carboxylic acids include without limitation benzoic acid herbicides, phenoxy carboxylic acid herbicides, pyridine carboxylic acid herbicides, and quinoline carboxylic acid herbicides. Examples of suitable benzoic acid herbicides include without limitation 2-methoxy-3,6-dichlorobenzoic acid (dicamba); 3,5,6-trichloro-o-anisic acid (tricamba); 3-amino-2,5-dichlorobenzoic acid (amiben); 5-2[2-chloro-4-(trifluoromethyl)phenoxy]-2-nitrobenzoic acid; 2,3,5-triiodobenzoic acid; and trichlorobenzoic acid; and the like. Examples of suitable phenoxy carboxylic acid herbicides include without limitation 2,4-dichlorophenoxyacetic acid (2,4-D); 2,4-dichlorophenoxybutyric acid (2,4-DP); 2-(2,4-dichlorophenoxy)propionic acid (2,4-DP); 2,4,5-trichlorophenoxyacetic acid (2,4,5-T); 2-(2,4,5-trichlorophenoxy)propionic acid; 4-chloro-2-methylphenoxyacetic acid (MCPA); 2-(4-chloro-2-methylphenoxy)propionic acid (MCPP); 4-(4-chloro-2-methylphenoxy)butyric acid (MCPD); 2-[4-(2',4'-dichlorophenoxy)phenoxy]propanoic acid; and the like. Examples of suitable pyridine carboxylic acid herbicides include without limitation 4-amino-3,5,6-trichloropicolinic acid (picloram); 3,5,6-trichloro-2-pyridinyloxyacetic acid (triclopyr); clopyralid; triclopyr; and the like. Examples of suitable quinoline carboxylic acid herbicides include without limitation quinclorac; quinmerac; and the like. Preferably, the carboxylic acid is dicamba.

Because the carboxylic acids are used in the melt form, the acids do not have to be dissolved in water. Thus the molten carboxylic acid is substantially free of water, thereby reducing the amount of water that must be removed in drying the salt. This in turn can provide cost benefits because less energy is required to dry the carboxylic acid salts. In addition, the water produced in the reaction vaporizes in the mixer 14 because of the temperatures in the mixer and the heat produced by the neutralization reaction, which also reduces the amount of drying that is needed. As used herein the term "carboxylic acids substantially free of water" refers to carboxylic acids in melt form and having less than about 10 percent, preferably less than about 2 percent, water content by weight.

Suitable alkaline compounds include alkali metal-containing compounds and ammonium-containing compounds known in the art. Examples of useful alkali metal-containing compounds include without limitation sodium hydroxide, potassium hydroxide, potassium carbonate, sodium carbonate, potassium bicarbonate, sodium bicarbonate, combinations thereof and the like. Preferably, the alkaline compound is provided as a sodium hydroxide or sodium bicarbonate solution and more preferably is an aqueous sodium hydroxide solution.

In the invention, the feed rates of the molten carboxylic acid and the alkaline compound are preferably controlled such that the alkaline compound entering mixer 14 substantially neutralizes the carboxylic acid. The degree of control of the molten carboxylic acid and alkaline compound feeds will depend on the feed devices used to feed the reactants into the mixer, the variation of the concentration of the reactant feeds, the titration curves for the acid, and other factors understood in the art. Typically, the molar amount of the alkaline compound fed to the mixer is within about 1%, preferably within 0.6%, of the molar amount sufficient to neutralize the carboxylic acid fed to the mixer. The amount of alkaline compound and the precision of the feed rate of the alkaline compound sufficient to neutralize the carboxylic acid within the desired pH limits can be determined by titration methods as would be well understood in the art. In a preferred embodiment of the invention, where molten dicamba and sodium hydroxide are used, these components enter the mixer 14 in a molar ratio of 1:0.97+/−0.6%, i.e., 1:0.964 to 1:0.976. The applicants have discovered that controlling the feed ratios of dicamba and sodium hydroxide within this range provides the benefit of producing sodium dicambate consistently having a pH between about 7 and about 9 when dissolved in water.

In this regard, as illustrated in FIG. 1, the ratio of the molten carboxylic acid feed and the alkaline compound feed can be precisely controlled using feed regulators (or metering devices) 20 and 22, respectively. Feed regulators 20 and 22 can be any of the types of devices known in the art to be useful for controlling the flow of a feed stream. Exemplary feed regulators include, without limitation, Coriolis flow meters, gear metering pumps, piston metering pumps, peristaltic pumps, diaphragm pumps, progressive cavity pumps, and the like. These pumps are known in the art and are commercially available. Preferably, Coriolis flow meters are used and communicate with a control system that maintains the ratio of the molten carboxylic acid feed and alkaline compound feed.

The carboxylic acid and the alkaline compound are metered into mixer 14 as described above. The feed rates of each of the carboxylic acid stream and the alkaline compound stream can vary as long as the molar amounts or molar ratios are maintained within the desired range. In other words, the carboxylic acid and alkaline compound are typically metered to the mixer 14 such that the alkaline compound is consistently within about 1%, preferably within 0.6%, of the molar amount sufficient to neutralize the carboxylic acid.

Typically, the reagents are maintained in the mixer 14 for a time sufficient and under conditions sufficient to mix the reagents and allow the reaction to begin and form a paste-like material. Because the neutralization reaction generally occurs at a rapid rate, most if not all of the neutralization reaction can occur in the mixer 14. Conditions within the mixer 14 may vary, depending upon the materials used, the product made, reaction temperatures., residence times, production rate and the equipment used. For example, the residence time of the carboxylic acid and alkaline compound within mixer 14 is selected to provide mixing and reaction of the reagents, and typically ranges from about 1 to about 10 minutes, preferably from about 2 to about 3 minutes. Preferably, the temperature is held below the decomposition temperature of the salt product and the decomposition temperature of the unreacted acid. For example, when using dicamba, the temperature within the mixer 14 is preferably maintained at about 90° C. to about 130° C., more preferably from about 100° C. to about 105° C. Pressure conditions in the mixer 14 may also vary although typically relatively low pressures can be used. The pressure can range from about full vacuum to about 100 psig, and preferably from about 0 psig to about 25 psig.

As illustrated in FIG. 1, in one advantageous embodiment of the invention, mixer 14 is a screw type extruder, although other mixing devices known in the art can be used. Examples of mixing devices useful in the present invention include without limitation single screw extruders, planetary gear extruders, twin screw co-rotating extruders, twin screw counter rotation extruders, kneader extruders, concentric screw mixer/extruders, reciprocating screw kneader/extruders, twin rotor continuous mix extruders, two stage mixer/extruders, disk extruders, transfer mixers, shear pumps, and the like.

The carboxylic acid salt formed in the reaction and any remaining carboxylic acid and alkaline compound are directed from mixer 14 to a suitable dryer, designated generally as 30 in FIG. 1. As illustrated in FIG. 1, the mixer 14 and the dryer 30 are separate units. Although FIG. 1 illustrates a pre-mixing step using mixer 14, the molten carboxylic acid and alkaline compound streams can be directly fed into dryer 30 without a pre-mixing step, as long as the dryer provides mixing of the reagents. However, it has been determined that for sticky materials that adhere to the dryer surfaces such as sodium dicambate, a mixer 14 has unexpectedly been found to be useful in providing the mixing of the reactants necessary to recover carboxylic acid salts from the dryer 30 having a consistent pH. It has been determined that when a mixer 14 is not used in these situations, even though the product may average the desired pH, the pH of the product is undesirably inconsistent. In particular, the salt particles formed by the reaction are not completely reacted with the outer portion of the particle being reacted and the inner portion of the particle being unreacted. As a result, samples of sodium dicambate recovered from the dryer 30 may vary between a pH of 5 and a pH of 11.

As mentioned above, water vapor is flashed off in the mixer 14 as a result of the mixer temperature and the heat produced by the neutralization reaction. Therefore, the connection between the mixer 14 and the dryer 30 preferably allows the passage of water vapor from the mixer to the dryer to prevent the build up of pressure in the mixer and to maintain the temperature of the reaction product at about the flash temperature (100° C.). Alternatively, the mixer 14 can include means for venting the water vapor.

Various dryers known in the art can be used in the process of the invention. Suitable, commercially available dryers include, for example, batch vacuum dryers, double drum dryers, thin film dryers, flash dryers, tumble dryers, spin-flash dryers, fluid bed dryers, and the like. Preferably, to produce sodium dicambate or other sticky or strongly adhering carboxylic acid salts, the dryer 30 is self-cleaning to advance any salts that form on the inside walls of the dryer through the dryer.

As illustrated in FIG. 1, the dryer 30 used in the preferred embodiment of the invention can be a horizontal cylindrical vessel. The dryer can be equipped with an external heating jacket (which can be heated using steam, hot oil, and the like). In addition, dryer 30 can include a central axially rotating shaft 32 fitted with a plurality of radially mounted mixing blades 34. Although illustrated with a single rotating shaft, the dryer 30 can also have two or more co- or counter-rotating shafts. The dryer 30 can also include additional mixing or kneading elements. For example, the dryer 30 can further include a plurality of stationary elements fixed to the inner wall of the dryer and capable of intermeshing with the rotating mixing blades 34 to provide good mixing of the reagents. The shaft and the stationary elements can also be hollow to increase the heating surface area for the dryer 30. The dryer 30 preferably provides suitable working or mixing of generally pasty, sticky, or viscous materials, particularly those such as sodium dicambate which strongly adhere to, cake onto or crust onto the interior surfaces (e.g. the heat transfer surfaces) of the dryer. Such dryers are known in the art and are commercially available, e.g., from LIST Inc. in Acton, Mass. and described, e.g., in U.S. Pat. Nos. 4,824,257; 4,826,324; 4,650,338; 4,889,431; 4,941,130; 4,950,081; 5,121,992; 5,147,135; 5,407,266; 5,823,674; 5,934,801 and 6,039,469.

One method of determining whether a carboxylic acid salt will cake onto or crust onto the inside surfaces of the dryer is to place the moist carboxylic acid salt in a stainless steel beaker, to load the salt with a weight to compact it and then to dry the carboxylic acid salt solution at the temperature and pressure at which the dryer is to be operated. The beaker can then be turned over to determine if a crust has formed on the beaker. If the dry, carboxylic acid salt sticks to the beaker then the carboxylic acid salt will form a crust in the dryer and a self-cleaning dryer should preferably be used. If a self-cleaning dryer is not used, then the dryer should preferably be operated at a temperature below the temperature at which a crust forms on the beaker. For example, if a salt is tested at different temperatures and forms a crust at 90° C. but not at 85° C., then a self-cleaning dryer is preferably used at drying temperatures at or above 90° C. and other dryers can be used at drying temperatures at or below 85° C.

The dryer 30 is operated under conditions that facilitate the removal of water and other solvents from the carboxylic acid salt to produce dry, carboxylic acid salt particles. Similar to the conditions of the mixer 14 discussed above, conditions within the dryer 30 may vary, depending upon the materials used, the product made, reaction temperatures, residence times, production rate and the equipment used. The dryer 30 is maintained at a temperature above the vaporization temperature of water and any other solvents used in the process but below the decomposition temperature of the carboxylic salt product. For example, when the carboxylic acid is dicamba, the temperature of the dryer 30 can range from about 110° C. to about 190° C., and is preferably about 160° C. Temperature ranges can be readily determined by the skilled artisan and will vary depending upon variables such as the types of solvent used, decomposition temperatures, and the like. As noted above, the dryer 30 can be provided with an external heating jacket suitable to heat the dryer using steam, hot oil, etc. Generally, for the salt to be produced in a useable form, water from the reaction (as well as any water or other solvents introduced into the reaction) must be substantially removed.

In accordance with a preferred embodiment of the invention, the inventors have found that the heat of neutralization, especially when strong acids such as dicamba are neutralized, can assist in drying the reaction product and removing the water produced in the neutralization reaction. As will be appreciated by the skilled artisan, the reaction of the molten carboxylic acid and the alkaline compound is an exothermic acid-base neutralization reaction in which the alkaline compound converts the molten carboxylic acid into a carboxylic acid salt and water. Maintaining the heat of neutralization in the process can in turn provide advantages in processing by reducing the energy required to heat the dryer 30. Thus, in the invention, the mixer 14 and the dryer 30 are preferably insulated so the heat of neutralization is substantially maintained in the reaction product.

The pressure of dryer 30 can vary and generally is maintained at ambient pressure, although the dryer can also be under vacuum to facilitate drying. Typically the pressure of the dryer 30 can range from about full vacuum to about 100 psig, and preferably from about 0 psig to about 25 psig.

Residence times within the dryer 30 are generally sufficient to substantially complete the reaction of the carboxylic acid and the alkaline compound, if necessary, and to remove water and other solvents to produce dry, carboxylic acid salt particles. Residence times can vary and typically range from about 5 to about 60 minutes, and preferably from about 10 to about 30 minutes.

Although not required, the dryer 30 can be continuously or intermittently flooded or purged with an inert fluid, such as nitrogen. This can aid in drying the reaction product. In addition, dryer 30 can be adapted to receive suitable monitoring devices to monitor temperature, pressure, and the like within the dryer, such as temperature indicators 36 in FIG. 1.

As illustrated in FIG. 1, the dryer can also include an overhead collection system 38 that includes a dust filter to recover dust and other byproducts generated by the reaction and exiting the dryer, and a condenser to condense water vapor driven off by the heat within the reactor. The dust, water vapor and other byproducts can be further treated downstream and disposed of by suitable methods known in the art. Pressure and temperature indicators, such as pressure indicator 40 and temperature indicator 42, can be present to monitor and control the pressure and temperature of the dust filter. The dust filter can also be continuously or intermittently purged with an inert fluid as indicated at 44.

The resultant dry, carboxylic acid salt particles can then be directed from dryer 30 to a suitable storage container 46, or the salt can be directed to additional downstream processing and packaging. As discussed above, the carboxylic acid salts of the invention are consistently produced at a desired pH and do not require blending or the use of buffers to produce the desired pH. Therefore, the carboxylic acid salts produced according to the invention can be immediately packaged and transported for use. For example, the sodium dicambate produced in accordance with a preferred embodiment of the present invention consistently has a pH between about 7 and about 9 when dissolved in water without requiring blending of salts or buffering of the salts to provide the desired pH.

Once the dry, carboxylic acid salt particles are produced, additional optional ingredients like water softening agents or surfactants can be added to the salt particles. In addition, the salt particles can be ground and/or screened to provide a herbicidal salt composition having the desired range of particle sizes (typically ranging from about 25 microns to about 5000 microns in diameter).

The salts prepared in accordance with the invention can have other advantageous physical properties, such as low water content, flowability, particle size, density, dustiness, and the like. Generally, the salts have less than about 5% by weight water, and preferably less than about 1% by weight water. Further, the salt composition dissolves essentially completely in water without agitation to provide a ready-to-use solution of the herbicidal salt.

The present invention will now be further described by the following non-limiting example.

EXAMPLE

Dicamba acid (2-methoxy-3,6-dichlorobenzoic acid) was melted, holding the jacket at no greater than 110° C.–115° C. The molten acid was pumped to the dryer, or to a twin screw extruder, which fed the dryer. 50% sodium hydroxide (caustic) was charged from another feed pot on a scale. The two ingredients were metered at controlled rates via a piston metering pump (acid) and a precise peristaltic pump (caustic). When combined, they formed a paste. The acid line was electrically traced to maintain a temperature of about 105° C. to 115° C. in the feed line. The paste was dried in the dryer either under vacuum or at atmospheric pressure with hot oil in the jacket. A slight nitrogen sweep was fed to the dryer. Overheads were condensed by a chilled water condenser, and by the liquid ring vacuum pump. The product was collected in a container designed to operate atmospherically or under vacuum.

The dicamba used was titrated with NaOH used at the pilot test. These results confirmed the lab titration using KOH. The KOH curve generated was shown to yield 28.87 ml for a pH of 7.0 and 29.27 ml for a pH of 9.0. The titrations reveal a weight ratio (base/acid) around 0.35 is to be used for a pH range of 7 to 9. This matched the used molar ratio (base/acid) 0.965 of theoretical.

It is understood that upon reading the above description of the present invention and reviewing the accompanying drawing, one skilled in the art could make changes and variations therefrom. These changes and variations are included in the spirit and scope of the following appended claims.

That which is claimed:

1. A method of making a dry, alkali metal or ammonium salt of a carboxylic acid, comprising the steps of:

feeding a molten carboxylic acid consisting essentially of dicamba and an alkali metal-containing or ammonium-containing alkaline compound in solution to a mixer;

reacting the molten dicamba and the alkali metal-containing or ammonium-containing alkaline compound to form an alkali metal or ammonium dicamba salt such that the dicamba is substantially neutralized to form a pasty, sticky material;

advancing the dicamba salt and any remaining dicamba or alkaline compound to a dryer;

removing water from the alkali metal or ammonium dicamba salt in the dryer to produce dry, alkali metal or ammonium dicamba salt particles; and recovering the dry, alkali metal or ammonium dicamba salt particles.

2. The method according to claim 1, wherein said feeding step comprises feeding the molten dicamba and alkaline compound in solution to the mixer such that the alkaline compound is consistently fed to the mixer in an amount within 0.6% of the molar amount sufficient to neutralize the dicamba fed to the mixer.

3. The method according to claim 1, wherein said reacting step comprises reacting the molten dicamba and the alkali metal-containing or ammonium-containing alkaline compound such that less than about 1% of the dicamba fed to the mixer remains after said reacting step.

4. The method according to claim 1, wherein the dicamba is neutralized in a single reacting step.

5. The method according to claim 1, wherein at least a portion of the reacting step occurs in the mixer.

6. The method according to claim 1, wherein substantially all of the reacting step occurs in the mixer such that less than about 1% of the dicamba fed to the mixer is advanced to the dryer.

7. The method according to claim 1, wherein said step of feeding the molten dicamba and the alkaline compound in solution to the mixer comprises:

metering the molten dicamba into the mixer; and metering the alkali metal-containing or ammonium-containing alkaline compound in solution into the mixer in an amount within about 1% of the molar amount sufficient to neutralize the dicamba.

8. The method according to claim 7, wherein said metering steps comprise metering the molten dicamba and the alkali metal-containing or ammonium-containing alkaline compound in solution into the mixer such that the amount of alkaline compound metered to the mixer is consistently within about 1% of the molar amount sufficient to neutralize the dicamba metered to the mixer.

9. The method according to claim 1, wherein said feeding step comprises mixing a molten dicamba that is substantially free of water with said alkaline compound.

10. The method according to claim 1, wherein said alkali metal-containing or ammonium-containing alkaline compound is sodium hydroxide, sodium bicarbonate, or a mixture thereof.

11. The method according to claim 1, wherein said reacting step comprises reacting the molten dicamba and alkaline compound in an insulated mixer thereby producing heat of neutralization and said removing step includes maintaining at least a portion of the heat of neutralization in the mixer and subsequently in the dryer to aid in removing water from the dicamba salt.

12. The method according to claim 1, wherein said removing step comprises removing water from the dicamba salt such that less than 5% by weight water remains in the dry, dicamba salts.

13. The method according to claim 1, wherein said removing step comprises removing water from the dicamba salt such that less than 1% by weight water remains in the dry, dicamba salts.

14. The method according to claim 1, wherein said removing step comprises heating the dryer to produce the dry, dicamba salt particles.

15. The method according to claim 1, wherein said removing step comprises drying the dicamba salt under vacuum.

16. The method according to claim 1, wherein said removing step comprises producing a nitrogen atmosphere in the dryer to aid the drying of the dicamba salt.

17. The method according to claim 1, wherein said advancing step comprises advancing the dicamba salt and any remaining dicamba and alkaline compound to a dryer that is self-cleaning thereby limiting the adherence of the dicamba salt to inside walls of the dryer.

18. A method of making sodium dicambate, comprising the steps of:
feeding to a mixer a molten carboxylic acid consisting essentially of dicamba and a solution of an alkaline sodium compound selected from sodium hydroxide, sodium bicarbonate and mixtures thereof, at a molar ratio of 1:0.97+/−0.6%;
mixing the molten dicamba and the alkaline sodium compound solution in the mixer;
reacting the molten dicamba and the alkaline sodium compound to produce a pasty, sticky reaction product comprising sodium dicambate;
advancing the sodium dicambate and any remaining dicamba and alkaline sodium compound to a dryer;
removing water from the sodium dicambate to produce dry, sodium dicambate particles; and
recovering the dry, sodium dicambate particles, said dry, sodium dicambate particles consistently having a pH between about 7 and about 9 when dissolved in water.

19. A method of making sodium dicambate, comprising the steps of:
metering a molten carboxylic acid consisting essentially of dicamba and that is substantially free of water to a mixer;
metering an aqueous sodium hydroxide solution to the mixer, said molten dicamba and sodium hydroxide being fed to the mixer at a substantially constant molar ratio of between 1:0.964 to 1:0.976;
mixing the molten dicamba and the aqueous sodium hydroxide to form a mixture; and
reacting the molten dicamba and sodium hydroxide to produce a pasty, sticky reaction product comprising sodium dicambate;
drying the sodium dicambate to produce dry, sodium dicambate particles; and
recovering the dry, sodium dicambate particles, said dry, sodium dicambate particles consistently having a pH between about 7 and about 9 when dissolved in water.

20. A method of making a dry, alkali metal or ammonium salt of a carboxylic acid, comprising the steps of:
feeding a molten carboxylic acid and an alkali metal-containing or ammonium-containing alkaline compound in solution to a screw type extruder;
reacting the molten carboxylic acid and the alkali metal-containing or ammonium-containing alkaline compound to form an alkali metal or ammonium carboxylic acid salt such that the carboxylic acid is substantially neutralized to form a pasty, sticky material;
advancing the carboxylic acid salt and any remaining carboxylic acid or alkaline compound to a dryer;
removing water from the alkali metal or ammonium carboxylic acid salt in the dryer to produce dry, alkali metal or ammonium carboxylic acid salt particles; and
recovering the dry, alkali metal or ammonium carboxylic acid salt particles.

21. A method of making a dry, alkali metal or ammonium salt of a carboxylic acid, comprising the steps of:
feeding a molten carboxylic acid and an alkali metal-containing or ammonium-containing alkaline compound in solution to a mixer;
reacting the molten carboxylic acid and the alkali metal-containing or ammonium-containing alkaline compound to form an alkali metal or ammonium carboxylic acid salt such that the carboxylic acid is substantially neutralized to form a pasty, sticky material; advancing the carboxylic acid salt and any remaining carboxylic acid or alkaline compound to a dryer comprising a rotating shaft fitted with a plurality of radially mounted mixing blades;
removing water from the alkali metal or ammonium carboxylic acid salt in the dryer to produce dry, alkali metal or ammonium carboxylic acid salt particles; and
recovering the dry, alkali metal or ammonium carboxylic acid salt particles.

22. The method according to claim 1, wherein said feeding step comprising feeding the molten dicamba and alkaline compound in solution to the mixer such that the alkaline compound is consistently fed to the mixer in an amount within about 1% of the molar amount sufficient to neutralize the dicamba fed to the mixer.

23. The method according to claim 1, wherein said method steps form a portion of a continuous process for making the dicamba salt.

24. The method according to claim 20, wherein said advancing step comprises advancing the carboxylic acid salt and any remaining carboxylic acid or alkaline compound to a dryer comprising a rotating shaft fitted with a plurality of radially mounted mixing blades.

25. The method of according to claim 20, wherein said feeding step comprises feeding a molten carboxylic acid consisting essentially of dicamba.

26. The method according to claim 21, wherein said feeding step comprises feeding a molten carboxylic acid consisting essentially of dicamba.

27. A method of making sodium dicambate, comprising the steps of:
    feeding to a screw-type extruder a molten carboxylic acid consisting essentially of dicamba and a solution of an alkaline sodium compound selected from sodium hydroxide, sodium bicarbonate and mixtures thereof;
    mixing the molten dicamba and the alkaline sodium compound solution in the screw-type extruder;
    reacting the molten dicamba and the alkaline sodium compound to produce a pasty, sticky reaction product comprising sodium dicambate;
    advancing the sodium dicambate and any remaining dicamba and alkaline sodium compound to a dryer comprising a rotating shaft fitted with a plurality of radially mounted mixing blades;
    removing water from the sodium dicambate to produce dry, sodium dicambate particles; and
    recovering the dry, sodium dicambate particles, said dry, sodium dicambate particles consistently having a pH between about 7 and about 9 when dissolved in water.

* * * * *